United States Patent
Møller

(10) Patent No.: US 12,032,230 B2
(45) Date of Patent: Jul. 9, 2024

(54) OPTICAL FILTER FOR SNOW CONDITIONS

(71) Applicant: Active Brands AS, Oslo (NO)

(72) Inventor: Ståle Norman Møller, Trysil (NO)

(73) Assignee: Active Brands AS, Oslo (NO)

( * ) Notice: Subject to any disclaimer, the term of this patent is extended or adjusted under 35 U.S.C. 154(b) by 522 days.

(21) Appl. No.: 17/292,111

(22) PCT Filed: Dec. 12, 2019

(86) PCT No.: PCT/EP2019/084918
§ 371 (c)(1),
(2) Date: May 7, 2021

(87) PCT Pub. No.: WO2020/120688
PCT Pub. Date: Jun. 18, 2020

(65) Prior Publication Data
US 2021/0397023 A1    Dec. 23, 2021

(30) Foreign Application Priority Data
Dec. 12, 2018    (NO) .................................. 20181594

(51) Int. Cl.
*G02C 7/10*    (2006.01)
*A61F 9/02*    (2006.01)

(52) U.S. Cl.
CPC .............. *G02C 7/104* (2013.01); *A61F 9/023* (2013.01)

(58) Field of Classification Search
CPC ................................ G02C 7/104; A61F 9/023
USPC ....................................................... 351/159.6
See application file for complete search history.

(56) References Cited

U.S. PATENT DOCUMENTS

| | | | | |
|---|---|---|---|---|
| 4,793,669 A | * | 12/1988 | Perilloux | G02B 5/282 359/359 |
| 5,646,781 A | * | 7/1997 | Johnson, Jr. | G02C 7/104 359/590 |
| 6,011,652 A | * | 1/2000 | Cushing | G02B 5/288 359/359 |
| 8,210,678 B1 | * | 7/2012 | Farwig | G02B 5/22 351/159.65 |
| 9,910,297 B1 | | 3/2018 | McCabe et al. | |
| 2006/0033851 A1 | | 2/2006 | Iori et al. | |

(Continued)

FOREIGN PATENT DOCUMENTS

| | | |
|---|---|---|
| EP | 2585870 B1 | 8/2018 |
| WO | WO-9720246 A1 | 6/1997 |
| WO | WO-0061043 A1 | 10/2000 |

(Continued)

OTHER PUBLICATIONS

Lingelbach, Bernd, et al.; "Contrast Enhancing Filters in Ski Sports"; Journal of ASTM International, vol. 2, No. 1; dated Jan. 2005; Paper ID JAI11972; 8 pages.

(Continued)

*Primary Examiner* — Sharrief I Broome
(74) *Attorney, Agent, or Firm* — Bradley Arant Boult Cummings LLP

(57) ABSTRACT

This invention relates to an optical filter for use in eyewear such as ski googles, as well as eyewear using the filter. For improving visibility in snow dominated locations, the filter has a transmission spectrum having a first transmission peak in the wavelength range of 620 nm-670, with a maximum at approximately 650 nm.

12 Claims, 3 Drawing Sheets

(56) References Cited

U.S. PATENT DOCUMENTS

2008/0094566 A1    4/2008  Ishak et al.
2013/0271725 A1*  10/2013  Chiou .................... G02C 7/12
                                                    351/159.56

FOREIGN PATENT DOCUMENTS

WO    WO-2014111099 A1    7/2014
WO    WO-2018019833 A1    2/2018

OTHER PUBLICATIONS

Girardin, François; International Search Report; PCT/EP2019/084918; dated Apr. 3, 2020; 4 pages.

* cited by examiner

OPTICAL FILTER FOR SNOW CONDITIONS

This invention relates to an optical filter especially for use in eyewear such as ski googles for improving visibility in snow dominated locations.

Snow googles and other types of eyewear such as sun glasses are frequently used to protect the eyes from the intense light on clear days and is especially important if the ground is covered with snow which also reflects ultraviolet light. The combination of bright sunlight and the reflected light may be dangerous to the eyes and cause snow blindness. In addition, even in cloudy weather the sensed contrast in the snow is very low and can cause difficulties, e.g. in downhill skiing where the skier has to be able to react fast as a response to any variations in the snow surface. For example, a patch of hard ice or a small pile of loose snow may be dangerous it the skier is caught unprepared at high speed.

Because of this several attempts has been made to filter the light so as to protect the eyes and improve the sensed contrast in the snow. This is one reason why ski googles may have different colors, trying to emphasize the parts of the spectrum where the contrast sensitivity is good by filtering the light transmitted through the googles.

One example of such a filtered eyewear is discussed in U.S. Pat. No. 9,910,297 where very high absorption (>80%) is provided in specific wavelengths, 550-570 nm and 450-490 nm. The chosen spectrum is, however, not suitable for distinguishing the different features in the snow and is not adapted to handle the increasingly warmer colors of a low sun at high latitudes. A filter for reducing phototoxic effect of shorter wavelengths is also described in US2008/094566, absorbing wavelengths in the range of 400-460 nm.

The object of the present invention is to provide a filter that both protect the eyes against ultraviolet light and improves a person's ability to distinguish contrasts in the snow.

According to the preferred embodiment of the invention the filter has two transmission peaks, one in the blue range, specifically in the range of 470 nm, or at least in the range of 460-500 nm.

The blue light transmission peak to create contrast in snow. The transmission peak at 470 nm is the most important transmission peak for seeing contrast in snow as it highlights wavelengths in blue to bluegreen.

It is well known that shorter wavelengths is scattered more efficiently than longer wavelengths in both air, as the sky is blue, and thus shadows and to some degree overcast weather may have a blue hue.

In a similar way water is blue because the absorption which gives water its color is in the red end of the visible spectrum. Therefore one sees blue, the complementary color of red, when observing light that has passed through several meters of water.

As with water, this color is caused by the absorption of both red and yellow light (leaving light at the blue end of the visible light spectrum). The absorption spectrum of ice is similar to that of water, except that hydrogen bonding causes all peaks to shift to lower energy—making the color greener. This effect is augmented by scattering within snow, which causes the light to travel an indirect path, providing more opportunity for absorption Larger grain sizes of bubbly ice allow deep penetration of incident light and a reflected hue that can vary from blue-green to blue depending on the color of the surface which underlies the ice. Thus improving the sensitivity of the skier for colours in the blue range may be advantageous.

Another concern when being outdoors is that blue light has a harmful effect as well and needs to be controlled. A Harvard medical study states that "High Energy Visible (HEV) blue light has been identified for years as the most dangerous light for the retina. After chronic exposure, one can expect to see long range growth in the number of macular degenerations, glaucomas, and retinal degenerative diseases". And a paper published by the American Macular Degeneration Foundation (AMDF) reports that "the blue rays of the spectrum seem to accelerate age-related macular degeneration (AMD) more than any other rays in the spectrum". Thus it may be advantageous to limit the amount of blue light, especially in the shorter wavelengths, reaching the skiers eyes.

As described above when light (or more specifically, packets of light called photons) from an astronomical object passes through the Earth's atmosphere, it scatters off particles in the latter. As shorter, "blue" wavelength scatter more than longer wavelengths the light penetrating the atmosphere will gradually contain less blue light and get a red hue. Because of this the light will contain more red light when sun is close to the horizon than when it is higher in the sky.

In the northern hemisphere you have the same effect in the middle of the winter. The sun stays lower in the horizon, and the sunlight becomes redder due to the long travel through the atmosphere. This shift is noticeable also in cloudy weather.

Thus it is an object of the present invention to provide eyewear suitable for use in winter sports, especially at high latitudes or in low sunlight, increasing the contrast and visibility in the wavelength ranges usual for sensing contrast in the snow and environment. This is obtained as specified in the accompanying claims.

The invention will be discussed below with reference to the accompanying drawings, illustrating the invention by way of examples.

Figure 1:
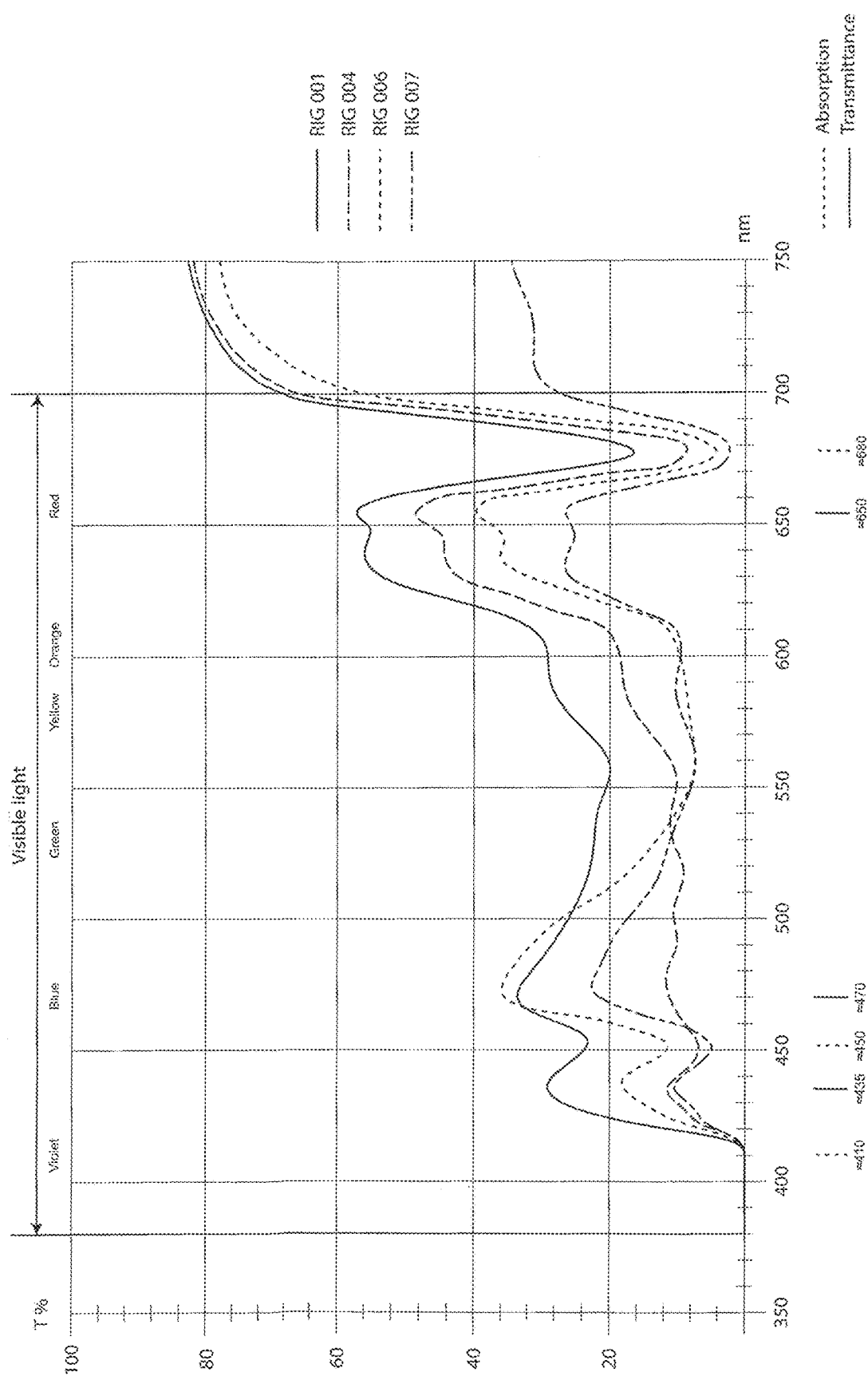
FIG. 1 illustrates four different transmission spectra for lenses according to the invention showing the transmission in percent as a function of the wavelength.

As can be seen from FIG. 1 all the filter spectra has a transmission peak, preferably at approximately 650 nm, or at least within the range of 620-670 nm, in order to increase the users sensitivity to the red light as discussed above. This way the ski goggles helps the user utilize the rad light from the sun being close to the horizon.

In order to boost in contrast in the red range the transmittance curve has a transmittance peak at 670 nm in order to capture most of the red sunlight being reflected off surfaces. It will also highlight red ski racing gates and red markings in the snow Also, the spectra have a relatively low transmission in the green and yellow parts of the spectrum, the first transmission peak being at least 2.5 times higher than the minimum transmission.

According to a preferred embodiment of the invention at least one additional transmission peak is present at 470 nm, or at least within the range of 460-500 nm, at least twice as high transmission as the minimum transmission in the 450-670 nm range. This is selected to increase the wearers sensitivity to the blue light distinguishing different types of ice, snow and water surfaces. Having a transmission peak in the blue end of the visible spectrum will thus create greater contrast in snow as the blue light is boosted, and less important colors has less transmission. The blue transmission peak will as well highlight blue ski racing gates as well as blue markings in the snow.

A third peak may also be implemented in the range of approximately 420-440 nm and especially at approximately 435 nm, with a local minimum between the second and third peaks at approximately 450 nm, in order to improve the ability to distinguish between the blue features, but in order to reduce the effects of HEV blue light the transmission is 0 below approximately 410 nm. Experimental evidence has suggested exposure to blue light in the 470-490 nm range may be less damaging compared to blue light from 400-470 nm. Thus in order to reduce the harmful blue light exposure the 435 nm peak may be lower than the peak at approximately 470 nm. As is shown in FIG. 1 the local minimum may have at least 10% reduction in the transmission when compared to the third peak. This may also depend on the chosen filter as well as the filter technology used to control the spectrum.

Figure 2:
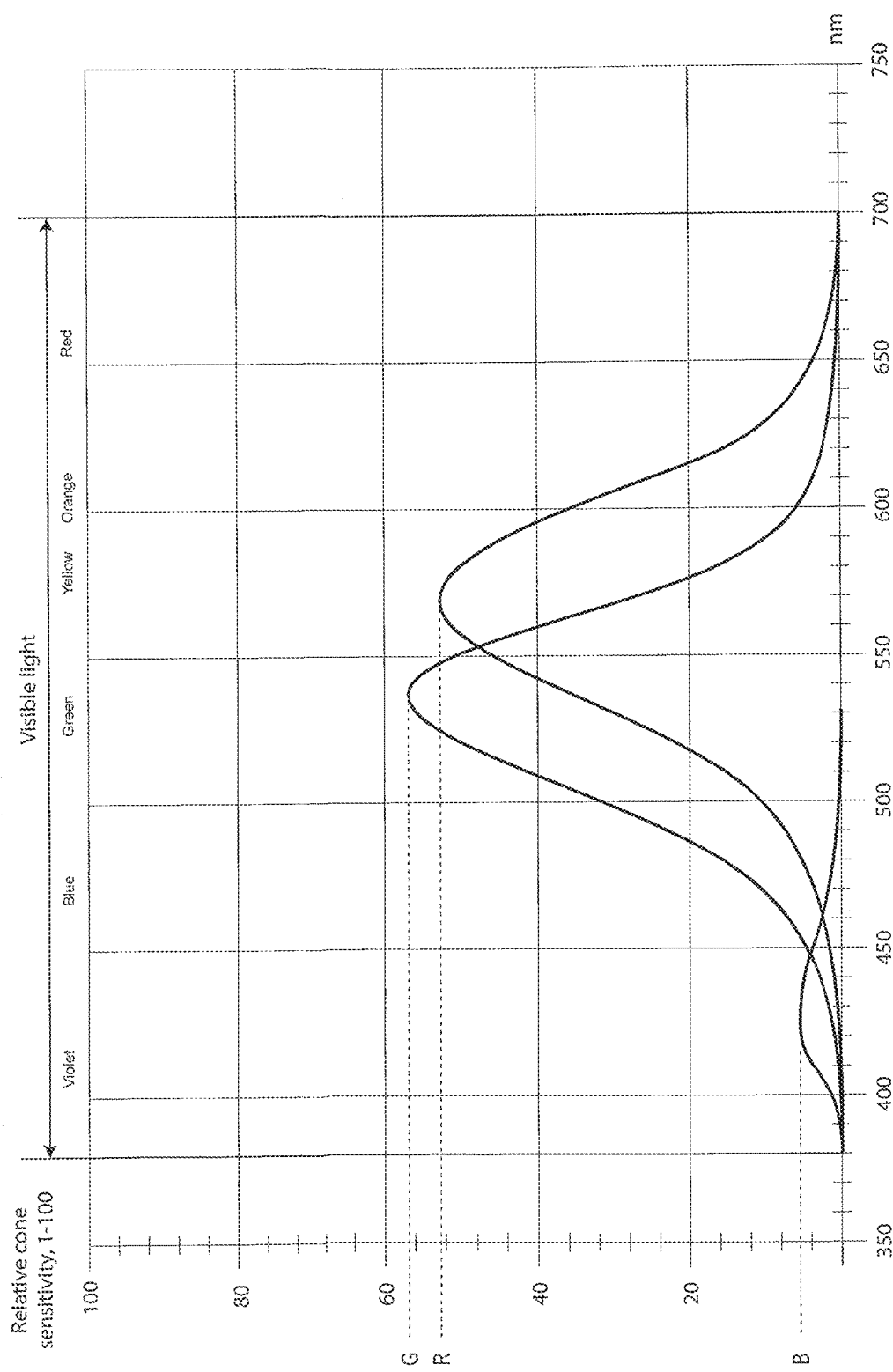
FIG. 2 illustrates the sensitivity spectrum of a human eye.

FIG. 2 illustrates the relative cone sensitivity on a comparable scale showing the blue, green and red sensitivity curves. As is evident from FIG. 3 where the preceding figures are combined the filter according to the present invention is attenuating the light in the range where the area where the eye has the highest sensitivity. In this way the user will experience an increased sensitivity, according to the preferred embodiment of the invention, in the ranges related to snow/water/ice surfaces as well as the red spectrum related to the low sun close to the horizon.

As discussed above, in order to have a transmission peak in the blue end of the visible spectrum while still staying safe, the transmission peak is at 470 nm which is what is considered to be in the safe region. The four different courves in FIG. 1 represent the following:

Lens "RIG 001" is based on extremely difficult light conditions which allows higher transmittance below 470 nm in order to boost contrast.

Transmittance curves described for "RIG 006" and "RIG 007" is developed for exposure to stronger light, thus has lower transmission below 470 nm Transmittance curve described for "RIG 004" is developed for even stronger light at higher altitude and has very little blue light transmission.

There is no transmission below 410 nm as light between 380 nm and 410 nm is considered harmful due to the high frequency There is no UV light (below 380 nm) transmission as UV light is known to be harmful.

While developing the lens technology, experiments were made with snow goggles which only transmitted blue and red wave lengths. This created a loss of depth perception as it is believed that all the three cones (R,G and B) need to be activated in order for the brain to receive enough information. Furthermore, a lot of snow lenses creates a monochrome sensation, usually in the yellow to red region. This is where the both R and G has relative high sensitivity (as is illustrated in FIG. 2) thus is perceived as bright and intensive light. It does not however create more contrast as there is very little of those colors available in snow environments. Therefore, the filter according to the invention maintains a transparency at all wavelengths above 410 nm with a transmission above 5% in the range between 420 and 670 nm.

Keeping some light transmission in the green and yellow wavelengths will also provide natural light and natural colors as well as providing great depth perception.

The transmittance curves are preferably obtained by mixing different biological stains with different absorption ranges within the visible light spectrum, but other structures such as dielectric coatings and diffractive patterns, e.g. as discussed in EP2585870B1, may be contemplated depending on the situation and the required accuracy of the transmission spectrum.

Figure 3:
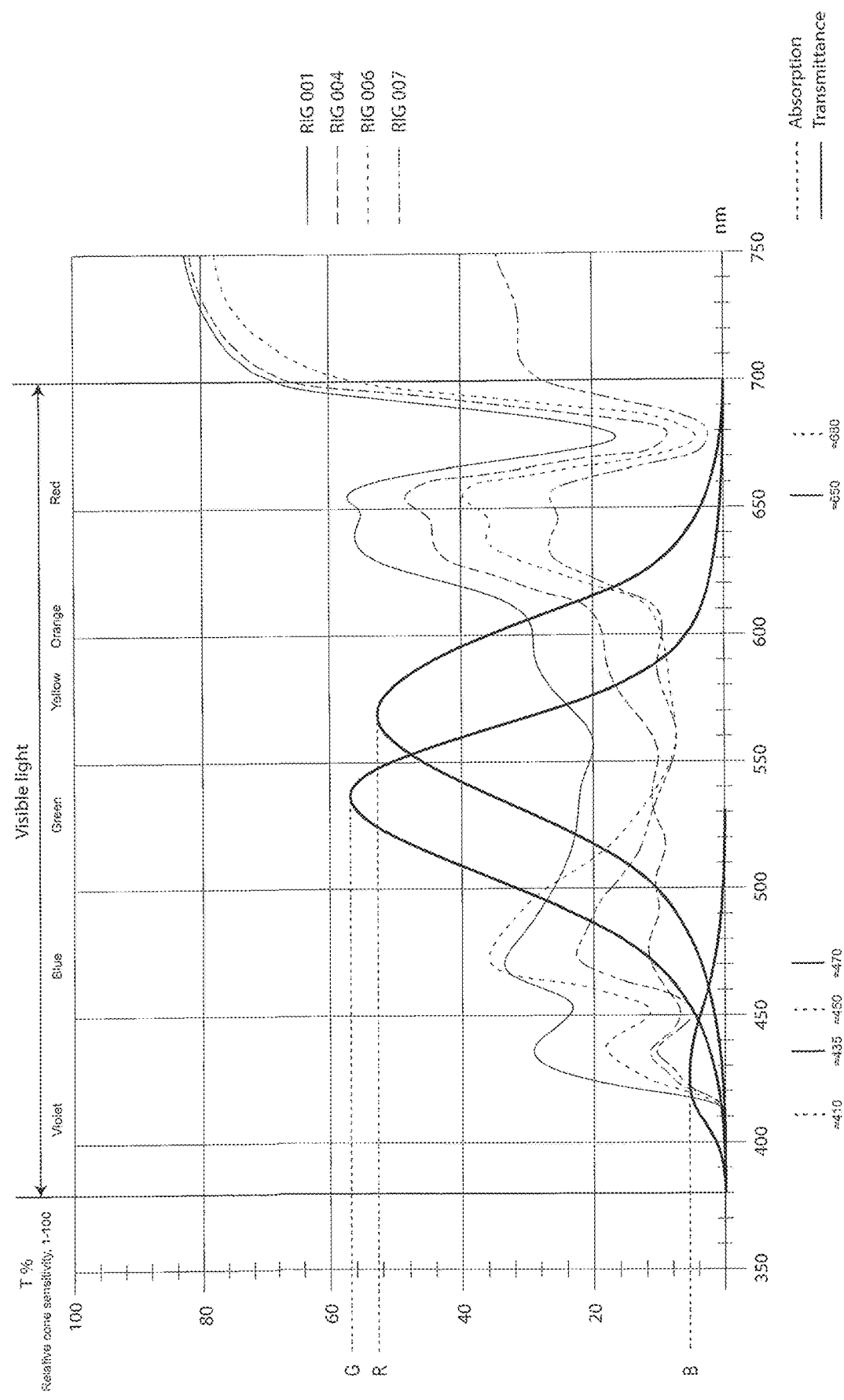
FIG. 3 illustrates the combination of FIGS. 1 and 2.

The absorption maximum at 680 nm shown in FIGS. 1 and 3 is a result of the production method in the specific case and does not have any significance for the performance filter at it is in the outskirts of the visual spectrum where the sensitivity of the eye is low. The essential feature being the transmission maximum at 650 nm.

To summarize the present invention relates to an optical filter for use in eyewear such as ski googles for improving visibility in snow dominated locations. The filter has a transmission spectrum with a first transmission peak in the wavelength range of 620 nm-670, with a maximum at approximately 650 nm. The ratio between the transmission peak value and the minimum transmission value in the range between 460-670 nm being at least 2.5.

The optical filter preferably also includes a second transmission peak in the range of 460-500 nm, with a maximum at approximately 470, where the ratio between the transmission peak value and the minimum transmission value in the range between 460-670 nm preferably is at least 2, but as seen in FIG. 1 with RIG 001 may be down to 1.5 depending on the situation. The first transmission peak thus preferably has a higher transmission than the second transmission peak.

The filter has a transmission in the complete spectrum between 420 nm and 670 nm with a minimum transmission in the range between 460 and 670 nm being at least 5-8% so as to provide the user with the full visual spectrum. Preferably the minimum transmission value in the range between in the range between 460 and 670 nm is more than ¼ of the first peak transmission maximum.

This way, in the preferred embodiment using two peaks the emphasis is made in the blue and red range while the light intensity in the green/yellow range is reduced.

In order to protect the users eyes the transmission is preferably reduced to zero below 410 nm, thus also stopping ultraviolet light and may be reduced in an even curve from the second transmission peak at 470 nm.

As discussed filter according to the present invention is especially suitable for use in eyewear for winter sports activities, such as ski googles, sun glasses etc.

The invention claimed is:

1. An optical filter for use in eyewear for improving visibility in snow dominated locations, the optical filter comprising:
   a transmission spectrum having a first transmission peak covering a wavelength range of 620-670 nm, with a maximum at approximately 650 nm, the ratio between the maximum transmission peak value and the minimum transmission value in the range between 460-670 nm being at least 2.5;
   wherein the spectrum includes a second transmission peak covering a range of 460-500 nm, with a maximum at approximately 470 nm, the ratio between the maximum transmission peak value of the second peak and the minimum transmission value in the range between 460-670 nm being at least 1.5;
   wherein the spectrum includes a third transmission peak covering a range of 420-440 nm with a maximum at approximately 435 nm and a local minimum in a range between 440 nm and 460 nm between the second and third peak; and wherein the minimum transmission value in the range between 460 nm and 670 nm is more than ¼ the first peak transmission maximum.

2. The optical filter according to claim 1, wherein the first transmission peak has a higher transmission than the second transmission peak.

3. The optical filter according to claim 1, wherein the local minimum between the second and third peak having at least 10% reduction in the transmission when compared to the third peak.

4. The optical filter according to claim 1, wherein the transmission is approximately zero below 410 nm.

5. The optical filter according to claim 1, wherein the minimum transmission between 460 and 670 nm is at least 5%.

6. The optical filter according to claim 1, wherein the filter is made from a mixture from biological stains with different absorption ranges within the visible light spectrum.

7. An optical filter optical filter for use in eyewear for improving visibility in snow dominated locations, the optical filter comprising: a transmission spectrum having a first transmission peak covering a wavelength range of 620-670 nm, with a maximum at approximately 650 nm, the ratio between the maximum transmission peak value and the minimum transmission value in the range between 460-670 nm being at least 2.5; wherein the spectrum includes a second transmission peak covering a range of 460-500 nm, with a maximum at approximately 470 nm, the ratio between the maximum transmission peak value of the second peak and the minimum transmission value in the range between 460-670 nm being at least 1.5; and wherein the spectrum includes a third transmission peak in the range of 420-440 nm with a peak at approximately 435 nm and a local minimum in the range between 440 nm and 460 nm between the second and third peak, the local minimum having at least 10% reduction in the transmission when compared to the third peak.

8. Eyewear comprising a filter according to claim 1.

9. Eyewear according to claim 8, wherein the eyewear is ski goggles.

10. The optical filter of claim 1, wherein the eyewear is ski goggles.

11. The optical filter according to claim 1, wherein the minimum between 440 nm and 460 nm is at 450 nm.

12. The optical filter according to claim 11, wherein the minimum between 440 nm and 460 nm has a reduction in the transmission of at least 10% when compared to the third peak.

* * * * *

UNITED STATES PATENT AND TRADEMARK OFFICE
CERTIFICATE OF CORRECTION

PATENT NO. : 12,032,230 B2
APPLICATION NO. : 17/292111
DATED : July 9, 2024
INVENTOR(S) : Ståle Norman Møller It is certified that error appears in the above-identified patent and that said Letters Patent is hereby corrected as shown below:

In the Claims

Claim 1, Column 5, Lines 1-3  Replace "wherein the minimum transmission value in the range between 460nm and 670nm is more than ¼ the first peak transmission maximum."
With --wherein the minimum transmission value in the range between 460nm and 670nm is more than ¼ of the first peak transmission maximum.--

Signed and Sealed this
Thirteenth Day of August, 2024

Katherine Kelly Vidal
*Director of the United States Patent and Trademark Office*